(12) United States Patent
Kanda (10) Patent No.: US 8,724,847 B2
(45) Date of Patent: May 13, 2014

(54) IMAGE PROCESSING APPARATUS AND PROGRAM STORAGE MEDIUM

(75) Inventor: Yamato Kanda, Hino (JP)

(73) Assignee: Olympus Corporation, Tokyo (JP)

( * ) Notice: Subject to any disclaimer, the term of this patent is extended or adjusted under 35 U.S.C. 154(b) by 226 days.

(21) Appl. No.: 12/831,551

(22) Filed: Jul. 7, 2010

(65) Prior Publication Data

US 2010/0272358 A1 Oct. 28, 2010

Related U.S. Application Data

(63) Continuation of application No. PCT/JP2008/071048, filed on Nov. 19, 2008.

(30) Foreign Application Priority Data

Jan. 8, 2008 (JP) ................................. 2008-001675

(51) Int. Cl.
*G06K 9/00* (2006.01)

(52) U.S. Cl.
USPC .......................................... 382/103; 382/128

(58) Field of Classification Search
USPC .......................................... 382/103, 128–134
See application file for complete search history.

(56) References Cited

U.S. PATENT DOCUMENTS

| | | | | |
|---|---|---|---|---|
| 4,396,903 A | * | 8/1983 | Habicht et al. ................. | 382/103 |
| 2004/0190607 A1 | * | 9/2004 | Wakimoto et al. ........ | 375/240.01 |
| 2004/0225223 A1 | | 11/2004 | Honda et al. | |
| 2005/0010106 A1 | * | 1/2005 | Lang et al. ..................... | 600/425 |
| 2005/0276446 A1 | * | 12/2005 | Chen et al. ..................... | 382/103 |
| 2007/0135715 A1 | | 6/2007 | Inoue et al. | |
| 2007/0165932 A1 | | 7/2007 | Nishimura et al. | |
| 2007/0292011 A1 | | 12/2007 | Nishimura et al. | |
| 2009/0074270 A1 | | 3/2009 | Tanaka et al. | |
| 2010/0002908 A1 | * | 1/2010 | Miyamoto et al. ............ | 382/103 |

FOREIGN PATENT DOCUMENTS

| | | |
|---|---|---|
| JP | 02-124131 | 5/1990 |
| JP | 2000-030058 A | 1/2000 |
| JP | 2000-048211 A | 2/2000 |
| JP | 2001-155167 A | 6/2001 |
| JP | 2004-086540 | 3/2004 |
| JP | 2005-332206 A | 12/2005 |
| JP | 2006-041648 A | 2/2006 |
| JP | 2006-288878 | 10/2006 |
| JP | 2006-320585 | 11/2006 |
| JP | 2006-334115 | 12/2006 |
| JP | 2006-334297 | 12/2006 |

(Continued)

OTHER PUBLICATIONS

International Search Report dated Jan. 13, 2009.

(Continued)

*Primary Examiner* — Alex Liew
(74) *Attorney, Agent, or Firm* — Scully, Scott, Murphy & Presser, P.C.

(57) ABSTRACT

An image processing apparatus according to an embodiment that processes time-series images that include a plurality of images captured in time series includes an interval setting unit that sets a time-series interval on the basis of a variation between images of the time-series images; and an area classifying unit that performs, in an image included in the time-series interval, classification into a plurality of category areas using a classification reference for each time-series interval set by the interval setting unit.

21 Claims, 8 Drawing Sheets

(56) References Cited

FOREIGN PATENT DOCUMENTS

| | | |
|---|---|---|
| JP | 2007-175432 | 7/2007 |
| JP | 2007-175434 | 7/2007 |
| JP | 2007-244519 | 9/2007 |
| JP | 2007-307395 | 11/2007 |
| JP | 2007-307396 | 11/2007 |

OTHER PUBLICATIONS

Japanese Office Action dated Dec. 13, 2011 from corresponding Japanese Patent Application No. JP 2008-001675 together with an English language translation.

Japanese Interrogation dated Aug. 14, 2012 from related application JP 2008-001675 together with an English language translation.

* cited by examiner

IMAGE PROCESSING APPARATUS AND PROGRAM STORAGE MEDIUM

CROSS-REFERENCE TO RELATED APPLICATIONS

This application is a continuation of PCT international application Ser. No. PCT/JP2008/071048 filed on Nov. 19, 2008 which designates the United States, incorporated herein by reference, and which claims the benefit of priority from Japanese Patent Application No. 2008-001675, filed on Jan. 8, 2008, incorporated herein by reference.

BACKGROUND OF THE INVENTION

1. Field of the Invention

The present invention relates to an image processing apparatus and a program storage medium for processing time-series images that include a plurality of images captured in time series.

2. Description of the Related Art

In recent years, a medical device as represented by a capsule endoscope, which sequentially captures images inside an intra-body canal such as an alimentary canal while moving inside the canal, has been developed. A capsule endoscope is swallowed from a mouth, is carried into a canal by using a peristalsis or the like, sequentially captures images at a predetermined capturing rate, transmits the captured images to an outside-body receiver, and is finally excreted outside the body. The number of captured time-series images is generally computed by a capturing rate (about 2 to 4 frames/sec) multiplied by an intra-body stay time (about 8 hours=8*60*60 seconds) of the capsule endoscope. The number of images is tens of thousands of sheets or more. A doctor spends a lot of time to check a great number of time-series images transmitted through the outside-body receiver by using a workstation for diagnosis or the like and specify a lesioned part. Thus, there is strongly desired a technology for improving the efficiency of the checking work of images performed by a doctor.

For example, Japanese Laid-open Patent Publication No. 2007-175432 discloses a method that divides time-series images captured by a capsule endoscope into multiple areas, such as mucous membrane, excrement, foam, and uncertainty. The method determines images that are unnecessary for observation and determines images that contain lesioned parts. Specifically, according to the method, each of images obtained by sampling time-series images at some intervals is divided into small sections, the small sections are mapped to a predetermined feature space such as an average color ratio space, and the mapped small sections are divided into clusters. Then, obtained clusters are classified into classes (categories) such as mucous membrane, excrement, and foam by using a classifier that is previously created on the basis of teacher data. Subsequently, the sampled images are divided into time-series-interval subsets. Occurrence frequency and distribution information of each class in each subset are calculated on the basis of the class classification result. Then, performed is classification, in the image in the time-series interval indicated by each subset, into class areas to detect a lesioned part on the basis of the calculation result.

SUMMARY OF THE INVENTION

An image processing apparatus according to an aspect of the present invention that processes time-series images that include a plurality of images captured in time series, includes: an interval setting unit that sets a time-series interval on the basis of a variation between images of the time-series images; and an area classifying unit that performs, in an image included in the time-series interval, classification into a plurality of category areas using a classification reference for each time-series interval set by the interval setting unit.

A program storage medium according to the present invention having stored thereon instructions that causes a computer, which processes time-series images that include a plurality of images captured in time series, to execute: an interval setting step of setting a time-series interval on the basis of a variation between images of the time-series images; and an area classifying step of performing, in an image included in the time-series interval, classification into a plurality of category areas using a classification reference for each time-series interval set by the interval setting step.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be explained below in detail with reference to the accompanying drawings. In the following explanations, it will be explained about an image processing apparatus that processes time-series images of an intra-body canal that are captured by a capsule endoscope in time series. However, time-series images that can be processed by the image processing apparatus of the present invention are not limited to the time-series images of the intra-body canal.

Embodiment

Figure 1:
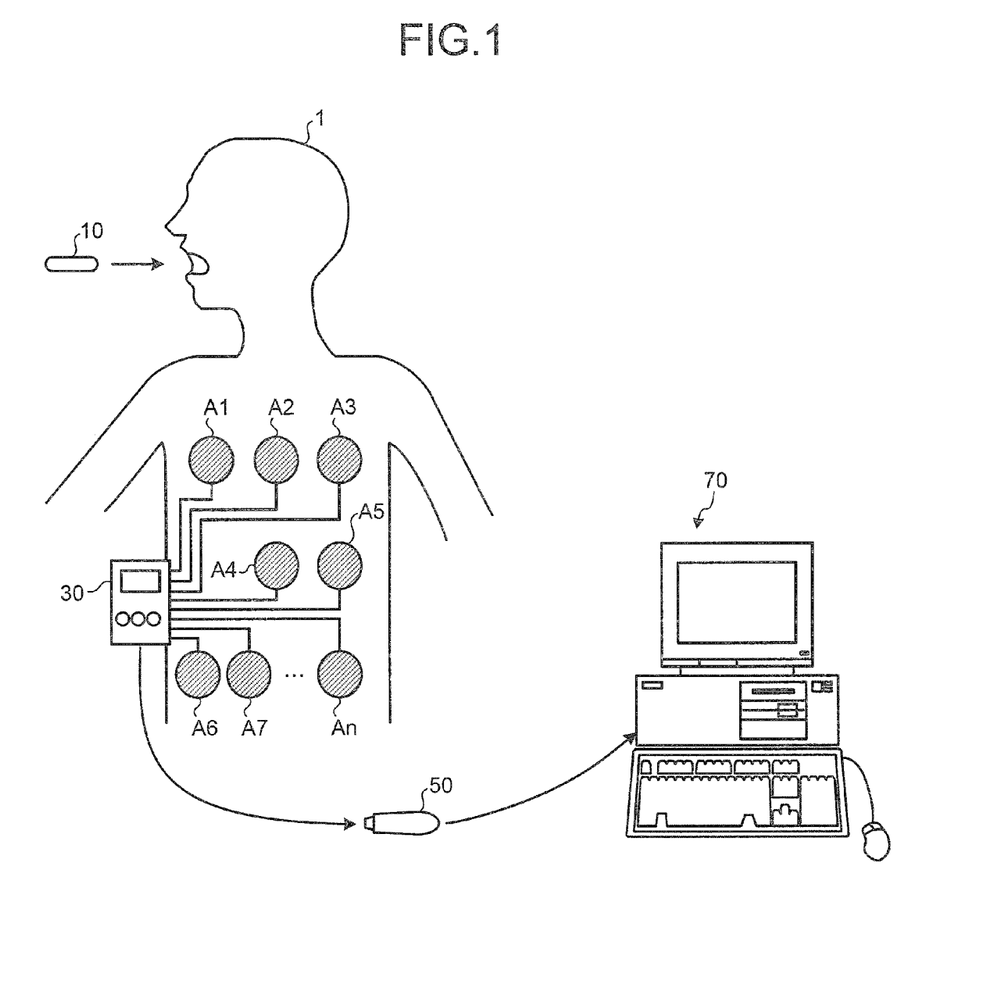
FIG. 1 is a schematic diagram illustrating the entire configuration of an image processing system that includes an image processing apparatus.

FIG. 1 is a schematic diagram illustrating the entire configuration of an image processing system that includes an image processing apparatus 70 according to the embodiment. As illustrated in FIG. 1, the image processing system includes a capsule endoscope 10 that captures images (hereinafter, "inside-canal images") of the inside of a subject 1, a receiving apparatus 30 that receives the inside-canal images transmitted from the capsule endoscope 10 by radio, the image processing apparatus 70 that processes and displays the inside-canal images captured by the capsule endoscope 10 on the basis of the inside-canal images received by the receiving apparatus 30. The delivery of image data between the receiving apparatus 30 and the image processing apparatus 70 is performed by, for example, a transportable recording medium 50.

The capsule endoscope 10 is a device that has an imaging function and a radio function. The capsule endoscope 10 is swallowed from the mouth of the subject 1 and is introduced into the subject 1, and sequentially captures inside-canal images while moving the inside of a body cavity. Then, the capsule endoscope 10 transmits the captured inside-canal images outside the body by radio.

The receiving apparatus 30 includes a plurality of receiving antennas A1 to An and receives the inside-canal images transmitted from the capsule endoscope 10 via the receiving antennas A1 to An by radio. The receiving apparatus 30 is configured to attach and detach the transportable recording medium 50 thereto and therefrom and sequentially saves image data of the received inside-canal images in the transportable recording medium 50. In this way, the inside-canal images of the inside of the subject 1 captured by the capsule endoscope 10 are accumulated in the transportable recording medium 50 by the receiving apparatus 30 in time sequence and are saved as time-series images.

The receiving antennas A1 to An are configured with, for example, loop antennas and adhere to the body surface the subject 1. Specifically, the receiving antennas are dispersed and arranged at positions corresponding to the passage path of the capsule endoscope 10 inside the subject 1. Incidentally, the receiving antennas A1 to An may be dispersed and arranged on a jacket that is worn by the subject 1. In this case, when the subject 1 wears the jacket, the receiving antennas A1 to An are arranged at predetermined positions on the body surface of the subject 1 corresponding to the passage path of the capsule endoscope 10 inside the subject 1. It is only necessary that the receiving apparatus 30 has one or more receiving antennas that are arranged on the subject 1. Therefore, the number of antennas is not limited to a certain number.

Figure 2:
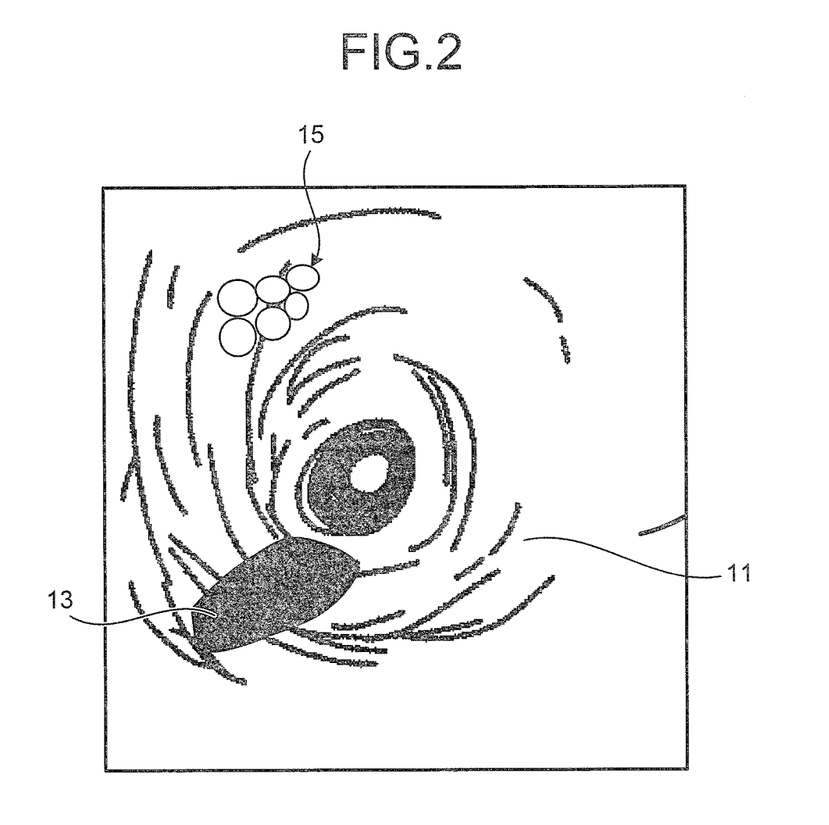
FIG. 2 is a diagram illustrating an example of an inside-canal image.

The image processing apparatus 70 is an apparatus that causes a doctor to observe and diagnose the inside-canal images captured by the capsule endoscope 10 and is realized with a general-purpose computer such as a workstation or a personal computer. The image processing apparatus 70 is configured to attach and detach the transportable recording medium 50 thereto and therefrom. The image processing apparatus 70 processes inside-canal images of time-series images saved in the transportable recording medium 50 and sequentially displays the images on a display such as LCD or ELD in time sequence. FIG. 2 is a diagram illustrating an example of an inside-canal image that is captured by the capsule endoscope 10 and is processed by the image processing apparatus 70. The inside-canal image includes a mucous membrane 11, a content 13 floating in the body cavity, foam 15, and the like, and further includes an important part such as a lesioned part in some cases. The inside-canal image captured by the capsule endoscope 10 is a color image that has the pixel levels (pixel values) of the color components of R (red), G (green), and B (blue) at each pixel position.

Figure 3:
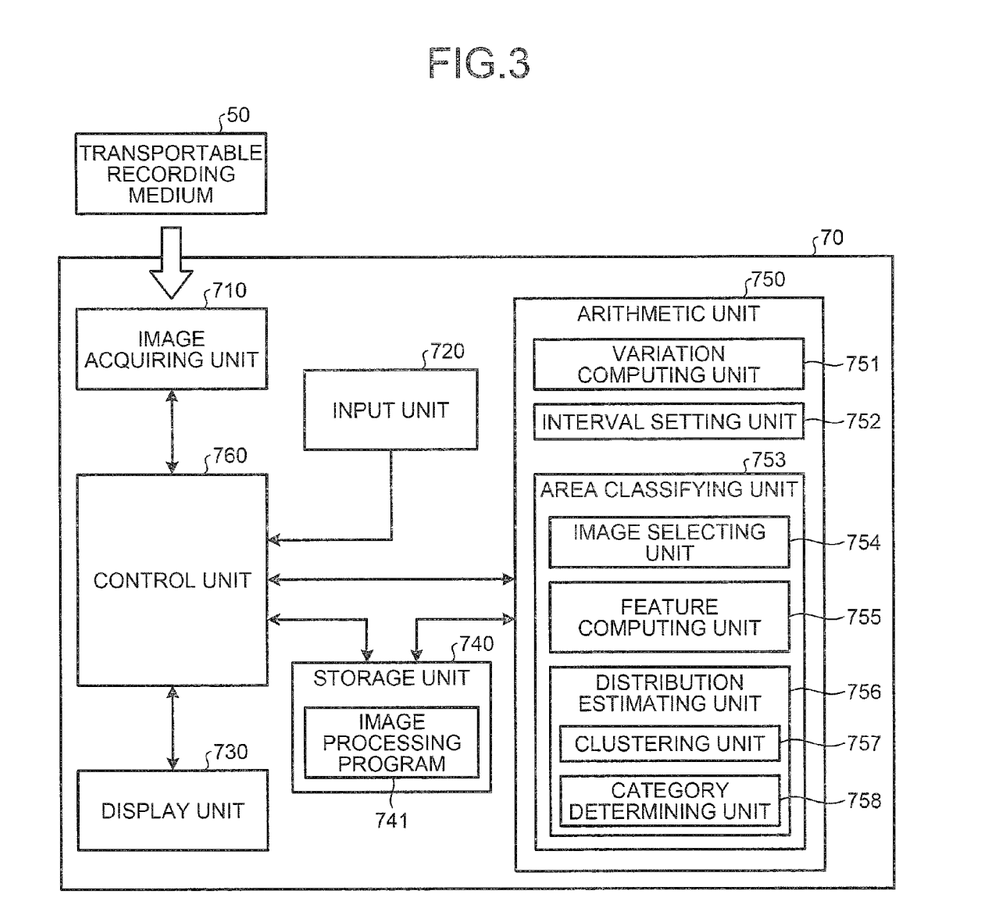
FIG. 3 is a block diagram explaining the functional configuration of the image processing apparatus.

FIG. 3 is a block diagram explaining the functional configuration of the image processing apparatus 70. In the present embodiment, the image processing apparatus 70 includes an image acquiring unit 710, an input unit 720, a display unit 730, a storage unit 740, an arithmetic unit 750, and a control unit 760 that controls the units of the apparatus.

The image acquiring unit 710 acquires inside-canal images of time-series images that are captured by the capsule endoscope 10 and are saved in the transportable recording medium 50 by the receiving apparatus 30. For example, the image acquiring unit 710 removably mounts thereon the transportable recording medium 50 and reads out and acquires the image data of inside-canal images accumulated in the mounted transportable recording medium 50. The image acquiring unit 710 is realized by, for example, a reading and writing device corresponding to the type of the transportable recording medium 50. It should be noted that a configuration for acquiring time-series inside-canal images captured by the capsule endoscope 10 is not limited to the configuration that employs the transportable recording medium 50. For example, a configuration may be adopted in which a hard disk is provided instead of the image acquiring unit 710 and the hard disk previously saves time-series inside-canal images captured by the capsule endoscope 10. Alternatively, a configuration may be adopted in which a separate server is provided instead of the transportable recording medium 50 and the server previously saves time-series inside-canal images. In such a case, the image acquiring unit includes a communication device for communicating with the server and the image processing apparatus is connected to the server via the image acquiring unit to acquire the time-series inside-canal images from the server.

The input unit 720 is realized by, for example, a keyboard, a mouse, a touch panel, or various types of switches and outputs an operation signal corresponding to an operation input to the control unit 760. The display unit 730 is realized by a display such as LCD or ELD and displays various types of screens including a screen for displaying time-series inside-canal images in accordance with the control of the control unit 760.

The storage unit 740 is realized by various types of IC memories that are ROM and RAM such as a flash memory that can be updated, an information recording medium such as a hard disk or CD-ROM that is embedded therein or connected by a data communication terminal, and a reader that reads them. The storage unit 740 stores a program related to the operation of the image processing apparatus 70, a program for realizing various functions included in the image processing apparatus 70, and data related to the execution of these programs. Moreover, the storage unit 740 stores an image processing program 741 for classifying inside-canal images of time-series images into category areas.

The arithmetic unit 750 is realized by hardware such as CPU. The arithmetic unit 750 sequentially processes the time-series inside-canal images acquired by the image acquiring unit 710 and performs various arithmetic processes for classifying the inside-canal images into the category areas. The arithmetic unit 750 includes: a variation computing unit 751 that functions as a variation computing means for computing a variation between a time-series inside-canal image captured by the capsule endoscope 10 that moves inside a canal and another image that is located near the time-series inside-canal image in a time-line; an interval setting unit 752 that functions as an interval setting means for setting a time-series interval on the basis of variations between images; and an area classifying unit 753 that functions as an area classifying means for performing, in the image included in the time-series interval, classification into a plurality of category areas such as "mucous membrane", "content", "foam", and "lesioned part" by using a classification reference for each time-series interval. Furthermore, the area classifying unit 753 includes: an image selecting unit 754 that functions as an image selecting means for selecting images from the time-series interval; a feature computing unit 755 that functions as a feature computing means for computing a feature from each image within the time-series interval; and a distribution estimating unit 756 that functions as a distribution estimating means for estimating a feature distribution of each category area located in the image included in the time-series interval. The distribution estimating unit 756 includes: a clustering unit 757 that functions as a clustering means for dividing the feature distribution of selected images that are selected by the image selecting unit 754 into clusters; and a category determining unit 758 that functions as a category determining means for determining the category of each cluster on the basis of the information of each cluster.

The control unit 760 is realized by hardware such as CPU. The control unit 760 transmits an instruction and data to each unit of the image processing apparatus 70 on the basis of image data input from the image acquiring unit 710, an operation signal input from the input unit 720, and a program and data stored in the storage unit 740 and overall controls the whole of the operations of the image processing apparatus 70.

Figure 4:
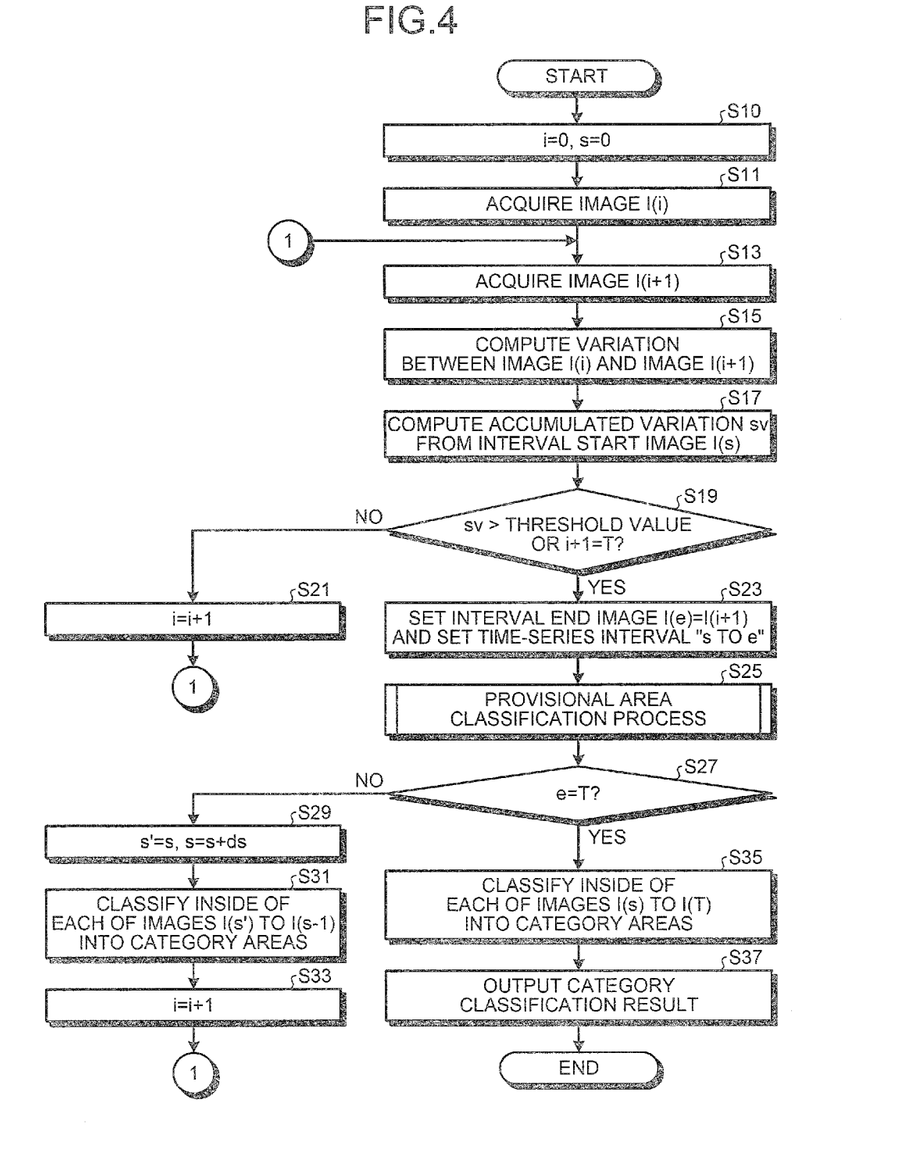
FIG. 4 is an entire flowchart illustrating a processing procedure performed by the image processing apparatus.

FIG. 4 is an entire flowchart illustrating a processing procedure performed by the image processing apparatus 70. The process explained in FIG. 4 is realized by executing the image processing program 741 stored in the storage unit 740 using the arithmetic unit 750. In FIG. 4, a flow when time-series images I(0) to I(T) of time-series sequence 0 to T are processed is illustrated.

As illustrated in FIG. 4, the arithmetic unit 750 first sets a symbol "i" that indicates the time-series sequence of an inside-canal image to be processed to zero and sets a symbol "s" that indicates the time-series sequence of a start image within a time-series interval to zero (Step S10). Next, the arithmetic unit 750 acquires an image I(i) that is an i-th inside-canal image in the time-series sequence (Step S11). Then, the arithmetic unit 750 acquires an image I(i+1) that is an (i+1)th inside-canal image serially located next to the image I(i) (Step S13).

Next, the variation computing unit 751 computes the variation between the image I(i) and the image I(i+1) (Step S15). There are various methods for computing a variation. As an example, the procedure of a method for comparing the corresponding areas between images is illustrated. First, images consisting of the G component of images I(i) and I(i+1) are acquired. The reason of using the G component is that the G component precisely indicates the contrasting information of an inside-canal image because the G component is close to the absorption wavelength band of hemoglobin in blood and has high sensitivity and resolution. Of course, other pixel values, values that indicate contrasting information secondly computed by well-known conversion, brightness (YCbCr conversion), or lightness (HSI conversion) may be used. Next, each G component image is divided into small sections that have a predetermined size. For example, the image is divided into m rows and n columns. Next, an average G component value is calculated for each divided small section. Then, the absolute value of the difference of the average G component values of the small sections located at the corresponding positions is calculated and the sum of all sections in the images is obtained as a variation v(i+1) in accordance with the following Equation (1).

$$v(i+1) = \sum_{m=1}^{M}\sum_{n=1}^{N} |G_{(m,n)}^{i} - G_{(m,n)}^{i+1}| \quad (1)$$

In this equation, $G_{(m,n)}^{i}$ is the G component average value of the small sections of m rows and n columns in the G component image of the image I(i). $G_{(m,n)}^{i+1}$ is the G component average value of the small sections of m rows and n columns in the G component image of the image I(i+1).

The variation reflects the movement of the capsule endoscope 10. The larger the value of the variation is, the more surrounding environment is different. In the above method, the sum of the absolute values of difference is indicated as a variation. Alternatively, the sum of squares of difference may be used. Moreover, a variation may be calculated by comparing the pixel values of pixels located at the corresponding positions without dividing images into small sections. Moreover, when using image data, such as JPEG, that is obtained by performing discrete cosine transform (DCT) on captured data in a section unit and performing compression encoding on the transformed data, a variation may be calculated by comparing DCT coefficients obtained for each unit section at the time of compression and extension or by comparing values secondly calculated from the DCT coefficients. Moreover, a variation may be calculated by comparing the amounts of statistics of pixel values between the images. For example, a variation may be calculated by comparing average values of R, G, and B components in images, standard deviation values of R, G, and B components in images, and histograms of R, G, and B components. Alternatively, a variation may be calculated by comparing average values or histograms of color ratios, color differences, hues, chroma saturations, or the like secondly calculated from R, G, and B component values. When using moving-image compressed data, such as MPEG, because the variations between images are computed and recorded at the time of compression encoding, these values may be utilized without performing the computation of variations between images. In this case, the variation computing unit 751 is not required.

Next, the interval setting unit 752 computes an accumulated variation "sv" that is a cumulative value obtained by accumulating variations from an interval start image I(s) in time sequence in accordance with the following Equation (2) (Step S17). Then, the interval setting unit 752 determines whether the computed accumulated variation sv exceeds a preset threshold value or whether the processed image I(i+1) is a final time-series image I(T) (Step S19).

$$sv = \sum_{k=s}^{i+1} v(k) \quad (2)$$

When the determination of Step S19 is No, the arithmetic unit 750 increments the symbol "i" that indicates the time-series sequence to be i=i+1 (Step S21) and returns the process control to Step S13. Conversely, when the determination is Yes, the interval setting unit 752 sets an interval end image I(e)=I(i+1) and sets a time-series interval "s to e" (Step S23).

Figure 5:
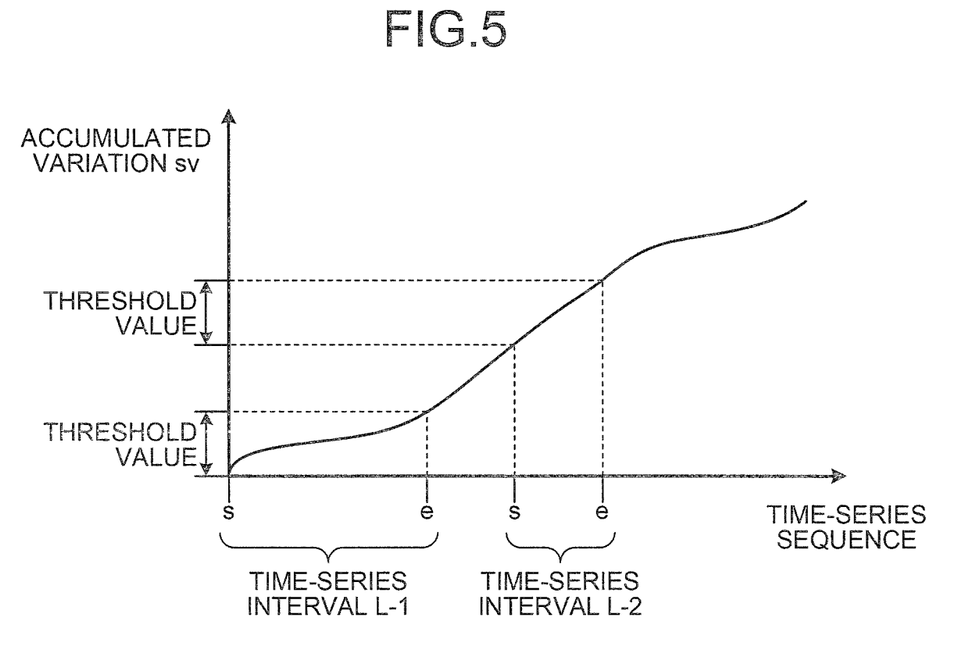
FIG. 5 is a diagram illustrating the situation of the setting of time-series intervals.

FIG. 5 is a diagram illustrating the situation of time-series interval setting. In FIG. 5, the transition of an accumulated variation sv is illustrated in which a horizontal axis is a time-series sequence and a vertical axis is an accumulated variation sv. Also, a time-series interval I-1, in which an inside-canal image of a time-series sequence i=0 is set as an interval start image I(s), and a time-series interval L-2, in which an inside-canal image of another time-series sequence i is set as an interval start image I(s), are illustrated. As illustrated in FIG. 5, because a time-series interval is set depending on whether the accumulated variation sv exceeds a threshold value, a long-time-series interval is set like the time-series interval L-1 when a variation between images is small and a short-time-series interval is set like the time-series interval L-2 when the variation is large. Although not illustrated, a time-series interval is also set in accordance with a predetermined threshold value between an interval end image I(e) of the time-series interval L-1 and the interval start image I(s) of the time-series interval L-2.

Figure 6:
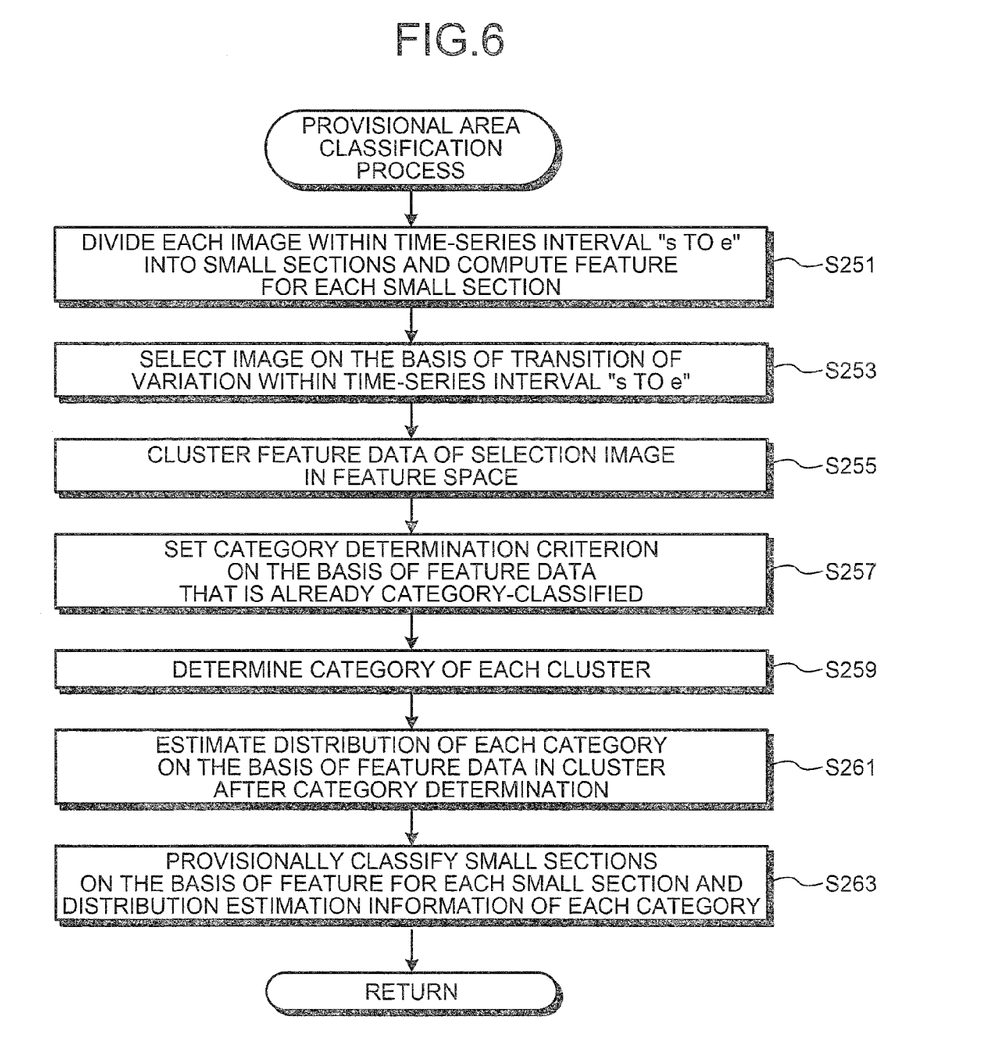
FIG. 6 is a flowchart illustrating the detailed procedure of a provisional area classification process.

After setting a time-series interval "s to e" in Step S23 of FIG. 4, the area classifying unit 753 performs a provisional area classification process and provisionally classifies the images I(j) (s≤j≤e) of the time-series interval "s to e" into category areas (Step S25). FIG. 6 is a flowchart illustrating the detailed procedure of a provisional area classification process.

In the provisional area classification process, the feature computing unit 755 first divides each image in the time-series interval "s to e" into small sections and computes a feature for each small section (Step S251). For example, the feature computing unit 755 divides an image into m rows and n columns and calculates, for each section, an average value, a standard deviation value, and a histogram of R, G, and B components, or an average value and a histogram of color ratios, color differences, hues, chroma saturations, or the like secondly calculated from R, G, and B component values. A special feature including a relationship with a peripheral pixel can be obtained by packing up pixels as a section that is a set of pixels instead of a single pixel. Moreover, like JPEG, when performing a discrete cosine transform (DCT) on captured data in a section unit and using the compression-encoded image data, a DCT coefficient calculated for each unit section at the time of compression and extension or a value secondly calculated from the DCT coefficient may be calculate as a feature.

Figure 7:
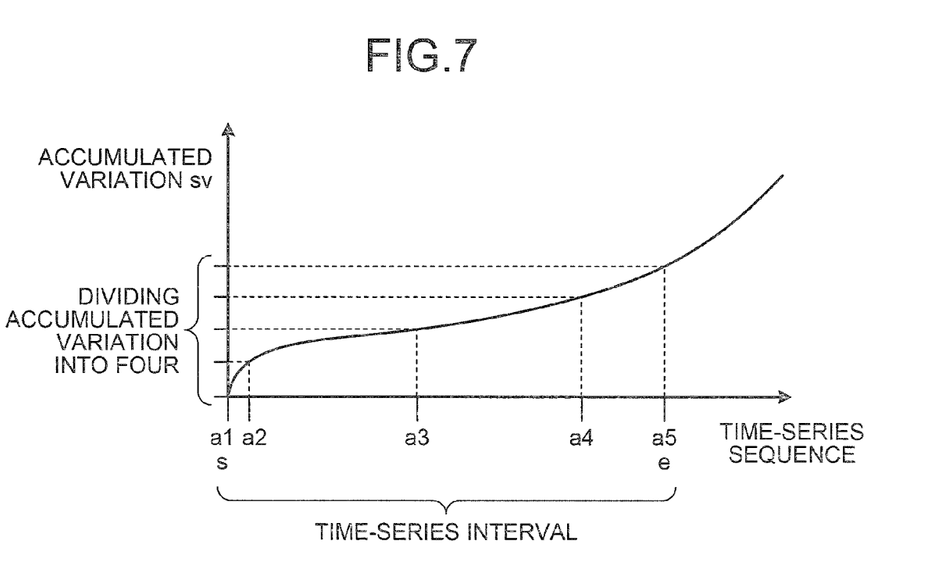
FIG. 7 is a diagram illustrating the situation of image selection.

Next, the image selecting unit 754 selects images on the basis of the transition of variation within the time-series interval "s to e" (Step S253). As a selection method, there is a method for first dividing accumulated variations within the time-series interval "s to e" into a predetermined number and then selecting images closest to accumulated variations corresponding to each division positions and interval start and end images. FIG. 7 is a diagram illustrating the situation of image selection. In FIG. 7, the transition of an accumulated variation sv is illustrated in which a horizontal axis is a time-series sequence and a vertical axis is an accumulated variation sv. Also, a time-series interval "s to e" in which the inside-canal image of a time-series sequence i=0 is set as an interval start image I(s) is illustrated. In FIG. 7, accumulated variations in the time-series interval "s to e" are divided into 4 and the images of time-series sequence a1 to a5 are selected as images closest to the division positions, an interval start image, and an interval end image. As described above, images are selected from the time-series interval "s to e" so as to have the same-degree variation between the images. Thus, the deflection of data in the subsequent category distribution estimation can be reduced. Incidentally, an image may be selected using a method for selecting an image of which the value of variation is not less than a predetermined threshold value, without using the accumulated variation.

Figure 8:
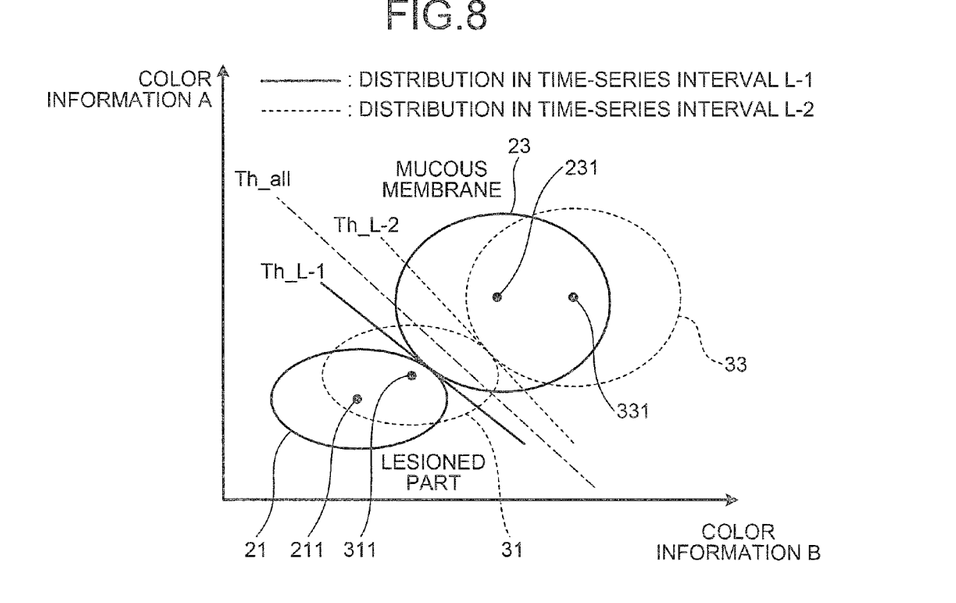
FIG. 8 is a diagram illustrating the effect of classification using clustering.

The image selecting unit 754 selects the images in the time-series interval "s to e" (hereinafter, the selected images are referred to as "selection images"). After that, as illustrated in FIG. 6, the clustering unit 757 clusters the feature data of the selection images in a feature space (Step S255). Clustering is a technique for dividing data distribution in the feature space. For example, well-known various techniques such as a hierarchical method, a k-means method, a self-organization map, and a technique disclosed in Japanese Laid-open Patent Publication No. 2007-175432 mentioned in BACKGROUND ART can be used. Now, it will be explained about the effect of clustering with reference to FIG. 8. FIG. 8 is a diagram illustrating the effect of classification using clustering. In an inside-canal image, the hues of a mucous membrane and a lesioned part are generally different. Thus, in the feature space that indicates color information as illustrated in FIG. 8, these areas respectively form clusters that have distributions different from each other. However, the distributions vary in accordance with the difference of a subject, an organ, or an interval inside a canal. In FIG. 8, an example of the distribution of "mucous membrane" and "lesioned part" performed on the images within the time-series interval L-1 illustrated in FIG. 5 is illustrated in a solid line and an example of the distribution of mucous membrane and lesioned part performed on the images within the time-series interval L-2 is illustrated in a broken line. If a discriminant criterion Th_all indicated by a chain line in FIG. 8 is used for classifying the distributions of "mucous membrane" and "lesioned part", for example, misclassification occurs for both of the time-series intervals L-1 and L-2. In the present embodiment, to solve this problem, each cluster is first obtained by clustering the feature data of selection images and dividing the clustered data. Then, the center of each cluster is determined in accordance with the discriminant criterion Th_all. Subsequently, the boundary between the clusters is set as a classification reference. With this, good classification can be performed for both of the time-series intervals L-1 and L-2. For example, for clusters 21 and 23 that are obtained by clustering the images within the time-series interval L-1 and indicated by the solid line of FIG. 8, centers 211 and 231 are first determined in accordance with the discriminant criterion Th_all. The center 231 is determined to be a mucous membrane and the center 211 is determined to be a lesioned part. Then, a boundary Th_L-1 between the clusters 21 and 23 is set as the classification reference of the time-series interval L-1. Similarly, a center 331 is determined to be a mucous membrane and a center 311 is determined to be a lesioned part in accordance with the discriminant criterion Th_all for clusters 31 and 33 that are obtained by clustering the images within the time-series interval L-2 and indicated by the broken line of FIG. 8. Then, a boundary Th_L-2 between the clusters 31 and 33 is set as the classification reference of the time-series interval L-2.

Figure 9:
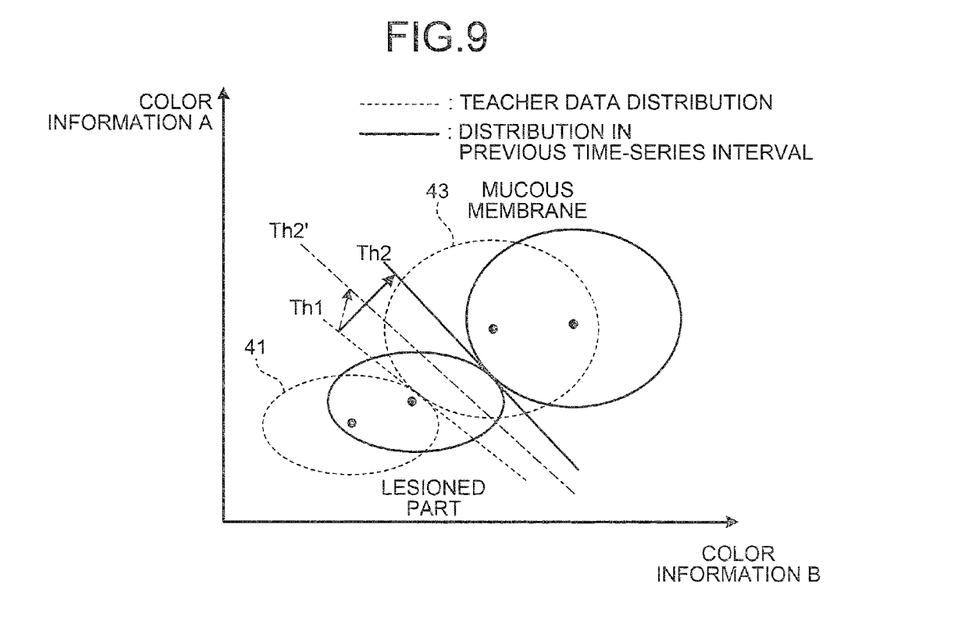
FIG. 9 is a diagram illustrating the updating of a category determination criterion.

As illustrated in FIG. 6, after clustering the feature data of the selection images, the category determining unit 758 sets a category determination criterion on the basis of the feature data that is already category-classified (Step S257). High-accuracy determination is performed by updating the discriminant criterion in conformity with the change of the feature distribution in time series. FIG. 9 is a diagram illustrating the updating of the category determination criterion. A discriminant criterion Th1 indicated by a broken line and used when processing the first time-series interval (L-1) is previously determined and saved in the storage unit 740 on the basis of teacher data that is indicated by broken lines 41 and 43 and preliminarily category-classified. Through each process step described below, the time-series interval is shifted. In the shifted time-series interval, a discriminant criterion to be applied is changed. Specifically, the discriminant criterion Th1, which is applied to the feature distribution of the first time-series interval that is the previous time-series interval, is changed into a discriminant criterion Th2 that can favorably classify the feature distribution indicated by the solid line. Alternatively, the discriminant criterion may be changed into Th2' that is indicated by the chain line of FIG. 9 and is located between the criterions Th1 and Th2. In FIG. 9, the discriminant criterion is illustrated by a hyperplane (a plane indicated by the linear equation of "the number of dimensions of the feature space−1", which is a straight line on a two-dimensional feature space as illustrated in FIG. 9) that determines two categories. The determination surface may not be a hyperplane. For example, a feature vector Fn=(fn_1, fn_2, . . ., fn_k)$^t$ of feature data included in each category distribution of teacher data is computed. Here, fn_i is the i-th feature value of n-th data and k is the number of dimensions of feature. Then, an average vector μ and a variance-covariance matrix Z are calculated on the basis of the obtained feature vector Fn in accordance with the following Equation (3).

$$\mu = \frac{1}{ND}\sum_{n=1}^{ND} Fn, \quad Z = \frac{1}{ND}\sum_{n=1}^{ND}(Fn-\mu)(Fn-\mu)^i \quad (3)$$

Next, a discriminant criterion that considers the distribution of categories can be set by setting a probability density function P for a multidimensional normal distribution that can be estimated from the values of the obtained average vector μ and variance-covariance matrix Z for each category in accordance with the following Equation (4).

$$P(x) = \frac{1}{(2\pi)^{K/2}\times|Z|^{1/2}}\exp\left\{(x-\mu)^i\times-\frac{1}{2}Z^{-1}\times(x-\mu)\right\} \quad (4)$$

Incidentally, |z| is the determinant of Z, $Z^{-1}$ is the inverse matrix of Z, and x is the feature vector of a determination target. The values of the obtained coefficients $$\frac{1}{(2\pi)^{K/2}\times|Z|^{1/2}}, \mu, -\frac{1}{2}Z^{-1}$$

and the occurrence probability of each category are stored in the storage unit 740.

Then, if the time-series interval is shifted, the discriminant criterion is updated by appending the feature of the data that is determined on a category in the previous time-series interval and performing calculation according to Equation (3) and Equation (4). The occurrence probability of each category can be calculated for every category in accordance with the number of areas of each category/the number of all areas.

After setting the discriminant criterion, the category determining unit 758 determines the category of each cluster as illustrated in FIG. 6 (Step S259). Specifically, the category determining unit 758 calculates the average vector of each cluster obtained by clustering. Next, the category determining unit 758 computes a probability P(x) by using the value of the obtained average vector as the feature vector x of the determination target indicated by Equation (4). Then, the category determining unit 758 calculates an attribution probability to each category that is obtained by multiplying the occurrence probability of each category and determines that a category having the largest probability is the category of each cluster.

Next, the distribution estimating unit 756 estimates the distribution of each category on the basis of the feature data in the cluster after category determination and calculates distribution estimation information (Step S261). This is a process corresponding to setting Th_L1 and Th_L2 in FIG. 8 and can be realized by performing calculation according to Equation (3) and Equation (4) on the basis of the data in each cluster. The occurrence probability of each category can be calculated by the number of areas of each category/the number of all areas for each category.

Next, the area classifying unit 753 provisionally classifies small sections on the basis of the feature obtained at Step S251 of the provisional area classification process for each small section of each image and the distribution estimation information of each category calculated at Step S261 (Step S263). Specifically, the area classifying unit 753 computes a probability P(x) by using a feature vector obtained for each small section as a feature vector x of the determination target indicated by Equation (4), calculates an attribution probability to each category that is obtained by multiplying the occurrence probability of each category by the probability P(x), and provisionally classifies it to a category that has the largest probability. At that time, the attribution probability is stored. After that, the process control is returned to Step S25 of FIG. 4 and then moves to Step S27.

When the provisional area classification process for provisionally classifying the images I(j) (s≤j≤e) of the time-series interval "s to e" into category areas is finished, the interval setting unit 752 determines whether an end image I(e) in the time-series interval is the final image I(T) of the time-series images (Step S27). When the determination is No, the start image sequence "s" of the time-series interval is stored as "s'". After that, a new start image sequence s=s+ds that is obtained by changing the start image sequence by a predetermined time-series width ds forwards is set (Step S29). When a feature distribution is estimated on the basis of the images within the time-series interval and the category classification is performed on the basis of the estimated result, the classification references for an interval start image and an interval end image that are the both ends of the time-series interval suddenly changes from the classification references for images that are continuous in time series. Therefore, for example, a new interval start image is set to necessarily overlap the time-series intervals by computing a time-series width in accordance with the following Equation (5). Then, the results obtained by performing provisional classification by the classification references of a plurality of time-series intervals that are overlapped are finally integrated for the time-series intervals and a classification result is calculated.

$$ds=0.5*(e-s+1) \quad (5)$$

From the viewpoint of a processing speed, ds may be ds=e−s+1 so that intervals are not overlapped at all.

Next, the area classifying unit 753 performs, in each image of images I(s') to I(s−1), classification into category areas (Step S31). As described above, to solve the discontinuity of classification references, provisional classification results for the overlapped time-series intervals are already obtained for the images I(s') to I(s−1) when time-series intervals are overlapped. Therefore, the final classification result is obtained for these images on the basis of the provisional classification results. When the overlapping width between intervals is large, one small section is processed in multiple time-series intervals. Multiple provisional classification results are obtained. In such a case, the classification is performed to select the most frequent category. Moreover, when there are two provisional classification results, a category in which a value corresponding to the certainty factor of classification, for example, an attribution probability to a category distribution or the like is larger may be selected as the final category. Then, the arithmetic unit 750 sets the symbol "i" that indicates the time-series sequence of an inside-canal image to be processed to "i=i+1" (Step S33), and then returns the process control to step S13 to repeatedly execute the process.

In contrast, when the determination performed at step S27 is Yes, in other words, when the interval end image of the time-series interval "s to e" is the final image of time-series images, the area classifying unit 753 performs, in each image of the images I(s) to I(T), classification into category areas (Step S35). This is a process similar to that of Step S31 except that images to be processed are different. Then, the arithmetic unit 750 outputs a category classification result for each image of the time-series images (Step S37), and terminates the process performed by the image processing apparatus 70. For example, the arithmetic unit 750 causes the display unit 730 to display the category classification result by transferring the result through the control unit 760.

As described above, according to the present embodiment, a time-series interval can be set such that the cumulative value of variations between images included in a time-series interval becomes a predetermined value. The classification, in the image included in the time-series interval, into category areas can be performed using the classification reference for each of the set time-series intervals. Thus, the classification in the image included in each time-series interval into category areas can be performed using an appropriate classification reference, and thus classification accuracy can be improved. Therefore, images of time-series images can be efficiently processed and a lesioned part can be detected from each image with high precision.

According to an image displaying apparatus of an embodiment, a time-series interval can be set on the basis of a variation between time-series images. Because the classification, in an image included in the set time-series interval, into category areas can be performed using a classification reference for each time-series interval, the classification accuracy of category area can be improved. Therefore, the classification in the time-series image can be efficiently performed with high precision.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus that processes time-series images that include a plurality of images captured in time series, the image processing apparatus comprising:
   an interval setting unit that sets a time-series interval on the basis of a variation between the plurality of images of the time-series images; and
   an area classifying unit that determines a category determination criterion for the time-series interval using a feature of an image in the time-series interval, the category determination criterion being common among the images in the time-series interval set by the interval setting unit and classifies each of at least a part of the plurality of images included in the time-series interval into a plurality of category areas using the category determination criterion.

2. The image processing apparatus according to claim 1, further comprising a variation computing unit that computes a variation between an image of the time-series images and another image located near the image in a time-line, wherein
   the interval setting unit sets the time-series interval on the basis of the variation computed by the variation computing unit.

3. The image processing apparatus according to claim 1, wherein
   the area classifying unit comprises:
   a feature computing unit that computes the feature of the image included in the time-series interval; and
   a distribution estimating unit that estimates a feature distribution of each category area located in the image included in the time-series interval on the basis of a feature distribution that is a distribution of the feature computed by the feature computing unit, and
   the area classifying unit performs, in the each of at least a part of the plurality of images included in the time-series interval, classification into the category areas on the basis of the feature distribution of each category area estimated by the distribution estimating unit.

4. The image processing apparatus according to claim 3, wherein
   the area classifying unit comprises an image selecting unit that selects an image from the time-series interval, and
   the distribution estimating unit estimates a feature distribution of each category area located in an image in the time-series interval on the basis of a feature distribution of the image selected by the image selecting unit.

5. The image processing apparatus according to claim 3, wherein
   the distribution estimating unit comprises:
   a clustering unit that divides the feature distribution that is the distribution of the feature computed by the feature computing unit; and
   a category determining unit that determines a category of each cluster obtained by the clustering unit, and
   the distribution estimating unit estimates the feature distribution of each category area on the basis of feature data of each cluster of which the category is determined by the category determining unit.

6. The image processing apparatus according to claim 1, wherein the interval setting unit sets the time-series interval on the basis of a cumulative value that is obtained by accumulating the variations between images in time sequence.

7. The image processing apparatus according to claim 1, wherein
   the interval setting unit sets the time-series intervals such that parts thereof are overlapped in a time-line, and
   the area classifying unit integrates classification results for the time-series intervals to perform, in an image included in the overlapped interval, classification into the category areas.

8. The image processing apparatus according to claim 4, wherein the image selecting unit selects an image on the basis of a variation between images.

9. The image processing apparatus according to claim 8, wherein the image selecting unit selects an image on the basis of a cumulative value that is obtained by accumulating the variations between images in time sequence.

10. The image processing apparatus according to claim 5, wherein the category determining unit changes the category determination criterion for each of the time-series intervals.

11. The image processing apparatus according to claim 2, wherein the variation computing unit computes a variation by comparing pixels or areas that positionally correspond between images.

12. The image processing apparatus according to claim 2, wherein the variation computing unit computes a variation by comparing amounts of statistics of pixel values.

13. The image processing apparatus according to claim 3, wherein the feature computing unit divides an image included in the time-series interval into a plurality of areas and computes a feature for each divided area.

14. The image processing apparatus according to claim 1, wherein the area classifying unit divides an image included in the time-series interval into a plurality of areas and performs category classification for each divided area.

15. The image processing apparatus according to claim 1, wherein the time-series images are images inside an intra-body canal.

16. The image processing apparatus according to claim 1, wherein the category areas include at least any one of a mucous membrane, a content, foam, and a lesioned part.

17. A program storage device having stored thereon instructions that causes a computer, which processes time-series images that include a plurality of images captured in time series, to execute:
   an interval setting step of setting a time-series interval on the basis of a variation between the plurality of images of the time-series images; and
   an area classifying step of determining a category determination criterion for the time-series interval using a feature of an image in the time-series interval, the category determination criterion being common among the images in the time-series interval set by the interval setting step and classifying each of at least a part of the plurality of images included in the time-series interval into a plurality of category areas using the category determination criterion.

18. An image processing method for processing time-series images that include a plurality of images captured in time series, the image processing method comprising steps of:
   setting a time-series interval on the basis of a variation between the plurality of images of the time-series images; and
   determining a category determination criterion for the time-series interval using a feature of an image in the time-series interval, the category determination criterion being common among the images in the time-series interval set by the interval setting step and classifying each of at least a part of the plurality of images included in the time-series interval into a plurality of category areas using the category determination criterion.

19. An image processing apparatus according to claim 1, wherein the area classifying unit sets the category determination criterion based on a plurality of images included in the time series interval.

20. The image processing apparatus according to claim 1, wherein the area classifying unit comprises:
   a feature computing unit that computes features of images included in the time-series interval; and
   a distribution estimating unit that estimates a feature distribution of each category area located in the images included in the time-series interval on the basis of a feature distribution that is a distribution of the features computed by the feature computing unit, and
   the area classifying unit performs, in the each of at least a part of the plurality of images included in the time-series interval, classification into the category areas on the basis of the feature distribution of each category area estimated by the distribution estimating unit.

21. The image processing apparatus according to claim 1, wherein:
   the interval setting unit sets a plurality of time-series intervals on the basis of variations between the plurality of images in the time-series images
   the category determining unit changes the category determination criterion among the time-series intervals.

* * * * *